(12) United States Patent
Stock et al.

(10) Patent No.: US 9,244,026 B2
(45) Date of Patent: Jan. 26, 2016

(54) X-RAY FLUORESCENCE ANALYZER

(71) Applicant: SCHLUMBERGER NORGE AS, Tananger (NO)

(72) Inventors: Tore Stock, Kleppe (NO); Egil Ronaes, Hundvag (NO); Thomas Hilton, Kirkland, WA (US)

( * ) Notice: Subject to any disclaimer, the term of this patent is extended or adjusted under 35 U.S.C. 154(b) by 39 days.

(21) Appl. No.: 13/852,960

(22) Filed: Mar. 28, 2013

(65) Prior Publication Data

US 2013/0235974 A1    Sep. 12, 2013

Related U.S. Application Data

(63) Continuation of application No. 13/578,274, filed as application No. PCT/US2011/024358 on Feb. 10, 2011, now abandoned.

(60) Provisional application No. 61/303,207, filed on Feb. 10, 2010, provisional application No. 61/308,076, filed on Feb. 25, 2010, provisional application No. 61/308,137, filed on Feb. 25, 2010, provisional application No. 61/370,541, filed on Aug. 4, 2010.

(51) Int. Cl.
  *G01N 23/22* (2006.01)
  *G01N 23/223* (2006.01)
  *G01N 33/28* (2006.01)

(52) U.S. Cl.
  CPC .......... *G01N 23/2204* (2013.01); *G01N 23/223* (2013.01); *G01N 33/2823* (2013.01); *G01N 2223/076* (2013.01)

(58) Field of Classification Search
  CPC .................. G01N 23/2204; G01N 23/223
  USPC ................................. 378/57, 47, 79
  See application file for complete search history.

(56) References Cited

U.S. PATENT DOCUMENTS

| 4,528,657 A | 7/1985 | Meehan |
| 6,012,325 A | 1/2000 | Ma |
| 6,111,930 A | 8/2000 | Schipper |
| 6,233,307 B1 * | 5/2001 | Golenhofen ................... 378/45 |
| 6,301,335 B1 | 10/2001 | Alfthan et al. |

(Continued)

FOREIGN PATENT DOCUMENTS

| CN | 101078696 A | 11/2007 |
| CN | 101158696 A | 4/2008 |

(Continued)

OTHER PUBLICATIONS

Halliburton Baroid, "Real-Time Mud Measurement", 2005, 16 pages.

(Continued)

*Primary Examiner* — Hoon Song

(57) ABSTRACT

An x-ray fluorescence apparatus for measuring properties of a sample fluid, the apparatus comprising a housing having an inlet and an outlet; a test chamber disposed within the housing, the test chamber comprising an injection port in fluid communication with the inlet; a slide disposed within the test chamber, the slide comprising a sample cavity; and a test port; an x-ray fluorescence spectrometer disposed within the housing, and at least one motor operatively coupled to the slide of the test chamber. Also, a method of testing a fluid, the method comprising injecting a fluid through an injection port of a test chamber into a sample cavity of a slide; moving the slide laterally within the test chamber to an intermediate position; moving the slide laterally within the test chamber to a test position; and actuating an x-ray fluorescence spectrometer to sample the fluid within the sample cavity when the slide is in the test position.

21 Claims, 6 Drawing Sheets

(56) References Cited

U.S. PATENT DOCUMENTS

| | | | |
|---|---|---|---|
| 6,668,039 | B2 | 12/2003 | Shepard et al. |
| 7,564,948 | B2 | 7/2009 | Wraight et al. |
| 2004/0234029 | A1* | 11/2004 | De Lange et al. ............... 378/70 |
| 2005/0031073 | A1 | 2/2005 | Radley et al. |
| 2007/0231217 | A1 | 10/2007 | Clinton et al. |
| 2009/0141862 | A1* | 6/2009 | Dunham et al. ............... 378/73 |

FOREIGN PATENT DOCUMENTS

| | | | |
|---|---|---|---|
| CN | 101498657 | A | 8/2009 |
| DE | 19911011 | A1 | 9/2000 |
| JP | 05256803 | A | 10/1993 |
| JP | 0823518 | B2 | 3/1996 |

OTHER PUBLICATIONS

Examination Report issued in AU2011215837 on Feb. 5, 2014, 2 pages.
Office Action issued in CN201180012999.6 on Mar. 31, 2014, 7 pages.
Office Action issued in EA201290766 on Jan. 13, 2014, 2 pages.
Office Action issued in EA201290766 on Nov. 27, 2014, 5 pages.
International Search Report and Written Opinion issued in PCT/US2011/024358 on Oct. 21, 2011, 9 pages.
"The Mud Watcher", Mud Automatics, retrieved from http://www.mudautomatics.com/Standard.aspx?id=18&pid=1;3;22, Accessed Aug. 19, 2014, 1 page.
Search Report issued in related EP application 11742798.9 on Nov. 17, 2015, 7 pages.

* cited by examiner

X-RAY FLUORESCENCE ANALYZER

BACKGROUND OF INVENTION

1. Field of the Invention

This application is a continuation of U.S. patent application No. 13/578,274, filed Aug. 10, 2012, which is a 371 of International Application PCT/US2011/024358, filed Feb. 10, 2011, both of which claim priority to and the benefit of provisional application U.S. 61/303,207 filed Feb. 10, 2010, provisional application US 61/308,076, filed Feb. 25, 2010, provisional application U.S. 61/308,137, filed Feb. 25, 2010 and provisional application U.S. 61/370,541, filed Aug. 4, 2010, all of which are hereby incorporated herein by reference in their entireties.

Embodiments disclosed herein relate to an x-ray fluorescence analyzer for use in determining drilling fluid properties. More specifically, embodiments disclosed herein relate to an x-ray fluorescence analyzer for use in determining drilling fluid properties at a drilling location in real-time. More specifically still, embodiments disclosed herein relate to methods and systems for determining drilling fluid properties that include automation and remote control.

2. Background Art

Wellbore drilling fluids serve many functions throughout the process of drilling for oil and gas. Primary functions include controlling subsurface pressures, transporting to the surface "cuttings" created by the drill bit, and cooling and lubricating the drill bit as it grinds through the earth's crust. Most of the cuttings are removed at the surface by different types of solids-removal equipment, by small bits of formation, such as clays and shales, are invariably incorporated into the drilling fluid as "low-gravity" solids. These low-gravity solids are generally undesirable in that they can contribute to excess viscosity and can adversely impact chemical treatment of the drilling fluid so that it can satisfy other critical functions. The low-gravity solids also are distinguished from high-gravity solids that are added intentionally to increase the density of the drilling fluid.

Fluid density, or mass per unit volume, controls subsurface pressures and contributes to the stability of the borehole by increasing the pressure exerted by the drilling fluid onto the surface of the formation downhole. The column of fluid in the borehole exerts hydrostatic pressure proportional to the true vertical depth of the hole and density of the fluid. Therefore, one can stabilize the borehole and prevent the undesirable inflow of formation fluids by maintaining a proper density of the drilling fluid to ensure that an adequate amount of hydrostatic pressure is maintained.

Several methods of controlling the density of wellbore fluids exist. One method adds dissolved salts such as sodium chloride and calcium chloride in the form of an aqueous brine to drilling fluids. Another method involves adding inert, high specific gravity particulates to drilling fluids to form a suspension of increased density. These inert high-density particulates are often referred to as "weighting agents" and typically include particulate minerals of barite, calcite, or hematite.

While maintaining the density of a drilling fluid is important, other factors also influence the effectiveness of specific drilling fluids in certain drilling operations. Such other factors may include viscosity and composition of the drilling fluid, as well as the fluids ability to cool and lubricate the drill bit. To determine the most effective drilling fluid for a given drilling operation, it is necessary to measure the chemical and physical properties of the drilling fluid as a returns from downhole.

Presently, the standard method for determining the liquid and solids content of the drilling fluid is to conduct a retort analysis. In a retort analysis, a drilling fluid sample is heated at sufficient temperature to vaporize contained liquids, including water, oil, or synthetics. The liquids are condensed, after which the specific volumes can be measured directly in a graduated cylinder. Oil and synthetics have a lower specific gravity than the water and will separate naturally in the measuring container. The total volume of liquids then is subtracted from the starting drilling volume to determine the total solids content. Appropriate mathematical functions are then applied in context of the general composition of the drilling fluid to estimate the fraction of high-gravity and low-gravity solids.

Due to the heating requirements, current retort practices are known to be potentially dangerous, and subject to inaccuracies and inconsistencies. Furthermore, the retort method does not provide means to characterize and differentiate the different solid components beyond the general categorization by gross specific gravity.

Accordingly, there exists a need for an automated method for determining drilling fluid properties.

SUMMARY OF INVENTION

In one aspect, the embodiments disclosed herein relate to an x-ray fluorescence apparatus for measuring properties of a sample fluid, the apparatus comprising a housing having an inlet and an outlet; a test chamber disposed within the housing, the test chamber comprising an injection port in fluid communication with the inlet; a slide disposed within the test chamber, the slide comprising a sample cavity; and a test port; an x-ray fluorescence spectrometer disposed within the housing, and at least one motor operatively coupled to the slide of the test chamber.

In another aspect, the embodiments disclosed herein relate to a method of testing a fluid, the method comprising injecting a fluid through an injection port of a test chamber into a sample cavity of a slide; moving the slide laterally within the test chamber to an intermediate position; moving the slide laterally within the test chamber to a test position; and actuating an x-ray fluorescence spectrometer to sample the fluid within the sample cavity when the slide is in the test position.

Other aspects and advantages of the invention will be apparent from the following description and the appended claims.

BRIEF DESCRIPTION OF DRAWINGS

FIG. 1 is a schematic representation of an XRF fluid analyzer according to embodiments of the present disclosure.

DETAILED DESCRIPTION

Figure 7:
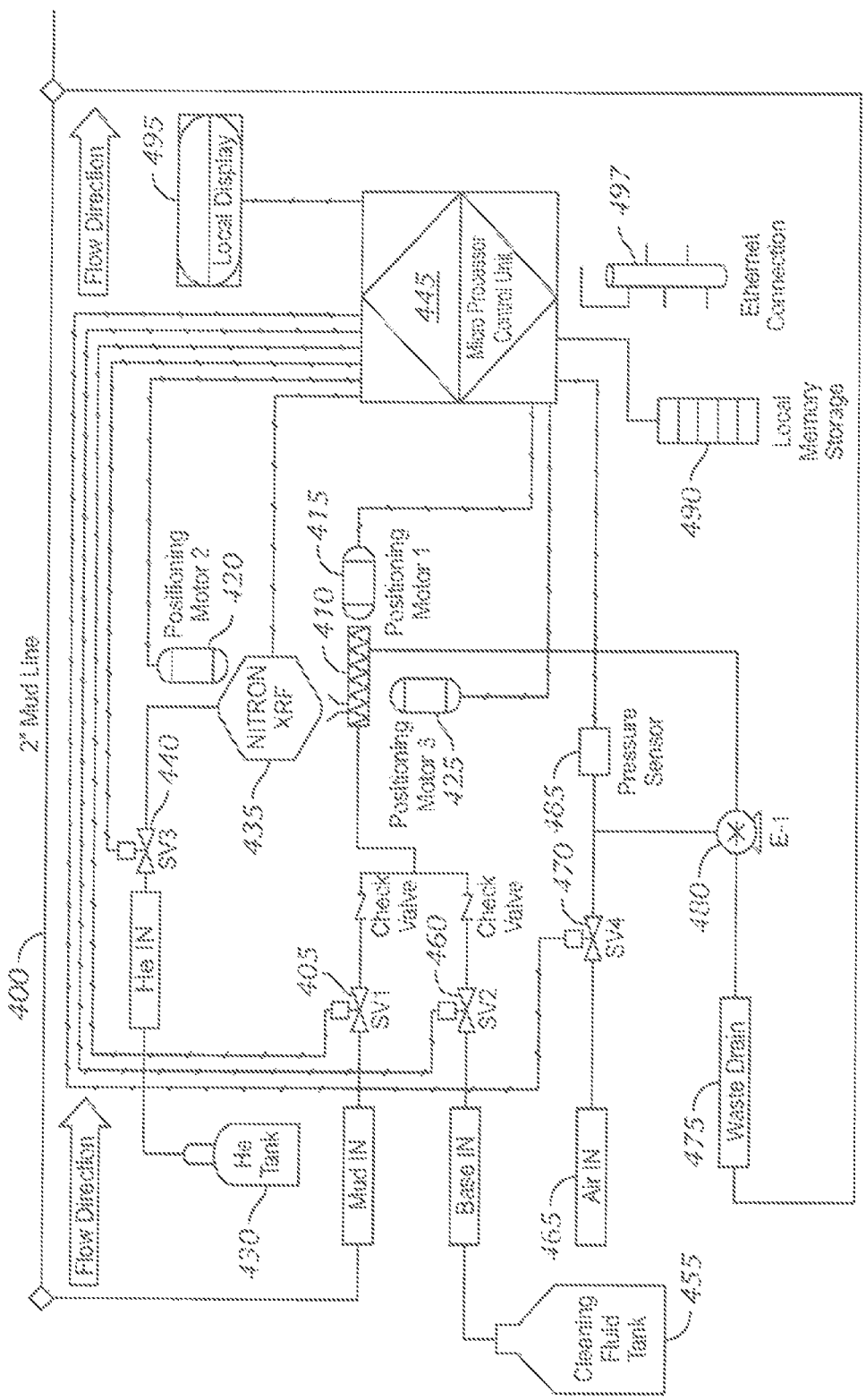

Embodiments disclosed herein relate to an x-ray fluorescence analyzer for use in determining drilling fluid properties.

More specifically, embodiments disclosed herein relate to an x-ray fluorescence analyzer for use in determining drilling fluid properties at a drilling location in real-time. More specifically still, embodiments disclosed herein relate to methods and systems for determining drilling fluid properties that include automation and remote control.

Embodiments disclosed herein also relate to a method and apparatus for automating the measurement of properties of invert emulsion oil-based or synthetic-based fluids (i.e., drilling fluids and/or completion fluids) and water based fluids. Although the disclosure herein may reference drilling fluid, one of ordinary skill in the art will appreciate that other types of fluids (e.g., completion fluids) may also be tested with the method and apparatus disclosed herein.

According to embodiments of the present disclosure, an x-ray spectrometer may be used to determine the content of a sample drilling fluid. For example, a sample may be excited by high energy x-rays or gamma rays, thereby causing the emission of secondary, fluorescent, x-rays. The secondary x-rays may then be analyzed to determine the chemical composition of the sample drilling fluid. The results of the testing may then be transferred to local storage or to a remote facility for processing. Those of ordinary skill in the art will appreciate that other meters may also be used to further analyze drilling fluid samples.

X-ray spectrometers ("XRF") according to embodiments of the present disclosure may be used to detect elements having an atomic weight as low as about 26.98, such as aluminum. In addition to aluminum, elements such as silicon, chlorine, potassium, calcium, bromine, caesium, barium, and the like may also be evaluated. The results of the XRF measurements may subsequently be linearly correlated with the concentration of the elements present in drilling fluids. Accordingly, the XRF analysis may be used to replace traditional titration tests. High-gravity solids measurement through barium analysis is also possible instead of using calculations from indirect measurements. Additionally, measurements of aluminum and silicon concentrations may be used in formation evaluation through trend analysis of sand and clay content. Those of ordinary skill in the art will appreciate that the XRF and automated XRF methods described below may generally be used to improve drill fluid measurements and increase the efficiency of drilling.

Referring to FIG. 1, a schematic representation of a fluid analyzer having an XRF 435 according to embodiments of the present disclosure is shown. In this embodiment, a flow of fluid is directed from an active drilling system flow line 400 through one or more valves 405, such as a check valve, a solenoid valve, or both, and into a test chamber 410. In still other embodiments, various actuated valves may be used alone or in addition to solenoid or check valves. Inside test chamber 410, a slide (450 of FIG. 2) is disposed and configured to move in one or more directions, thereby allowing a sample of drilling fluid to be procured from the active fluid system. One or more motors 415, 420, and 425 may be used to control the orientation of the slide or test chamber 410. As illustrated, motor 415 is configured to move slide laterally in test chamber 410. However, in other embodiments, motor 415 may be used to move slide in more than one direction. The fluid analyzer also includes a helium tank 430 in fluid communication with XRF 435, thereby allowing helium to be used during the analysis. In order to control the flow of helium from helium tank 430 to XRF 435, a solenoid valve 440 may be operatively controlled by a micro processor 445 or PLC.

Figure 1A:
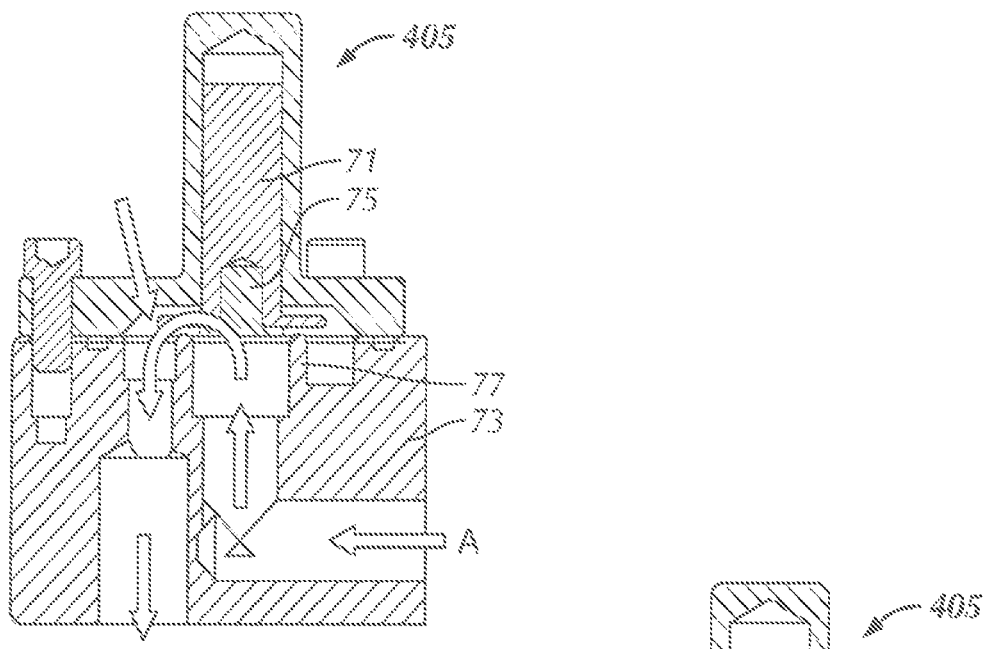
FIGS. 1A and 1B are cross-sectional views of a check valve according to embodiments of the present disclosure.
Figure 1B:
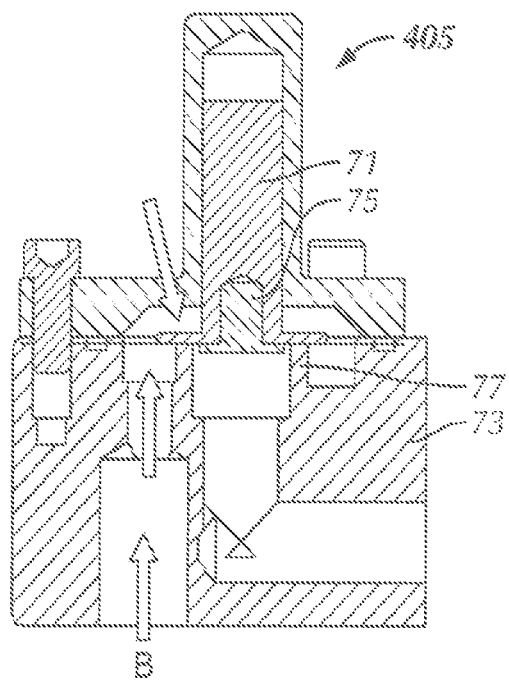
Figure 1C:
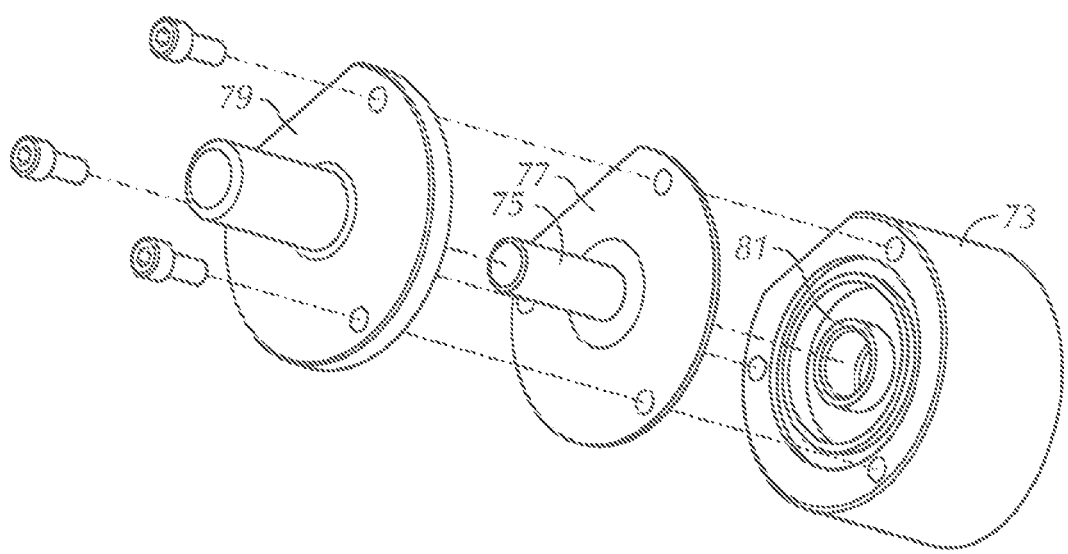
FIG. 1C is an exploded view of a check valve according to embodiments of the present disclosure.

Referring briefly to FIGS. 1A and 1B, an alternative valve 405 according to embodiments of the present disclosure is shown. In FIG. 1A, a check valve 405 is shown. The check valve 405 includes a plunger 71, a valve body 73, and a plunger assembly 75 including an elastomer material 77. During a fill stage of the testing (FIG. 3A), during low pressure conditions, the fluid is flowing along path A, thereby moving the plunger 71 into an open position and allowing fluid to flow into the electrical stability meter. During a high pressure condition, such as during a back flow, the fluid is flowing in direction B (of FIG. 3B), causing the plunger 71 to close and seal check valve 405. Such a one-way check valve may be less prone to failure from liquids or slurries that are highly viscous or contain particulate matter. Referring briefly to FIG. 1C, an exploded view of valve 405 is shown. As illustrated, check valve 405 includes a valve body 73, a plunder assembly 75 having an elastomer material 77, and a plunger guide 79. The elastomer material 77 is configured to seal against sealing surface 81 of valve body 73, and is configured to remain constrained within plunger guide 79.

Referring back to FIG. 1, the fluid analyzer may also include a cleaning fluid tank 455 in fluid communication with test chamber 410. During a cleaning cycle, a fluid, such as a base oil, water, or other fluid containing chemicals such as surfactants may be transferred from the cleaning fluid tank 455 to the test chamber 410. The flow of the cleaning fluid may be controlled by a valve, such as solenoid valve 460. In addition to cleaning fluid, fluid analyzer may include an air system 465 configured to supply air to test chamber 410 or another component of the fluid analyzer. The flow of air may also be controlled with a valve, such as a solenoid valve 470. After a test is complete, the sample fluid may be drained from test chamber 410 through waste drain 475 and back into the active drilling system flow line 400. The sample fluid evacuation may be facilitated though use of a pump 480, air from air system 465, or pushed out of test chamber 410 as new fluid is drawn into test chamber 410. The fluid analyzer may also include various sensors, such as pressure sensor 485, temperature sensors (not shown), or other various sensors for determining the position of the slide within test chamber 410 or a property of the fluid.

To control fluid analyzer, the system includes micro processor 445 and a local memory storage 490, such as a hard disc drive, flash, or other type of memory known in the art. Data may be displayed and the fluid analyzer may be controlled through local display 495. Additionally, a device for allowing a connection to a network, such as a modem 497, may be used to allow the fluid analyzer to communicate data as well as receive control signals remotely. The remote control aspect of the present disclosure will be explained in detail below.

Figure 2A:
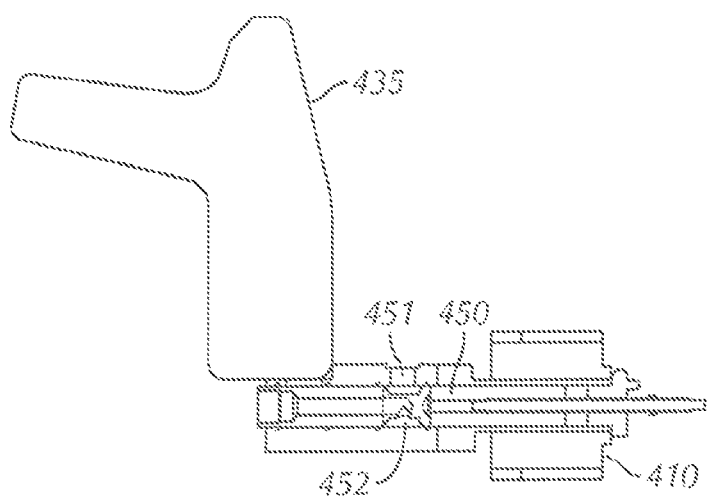
FIGS. 2A-C are cross-sectional views of a test chamber of the XRF analyzer according to embodiments of the present disclosure.
Figure 2B:
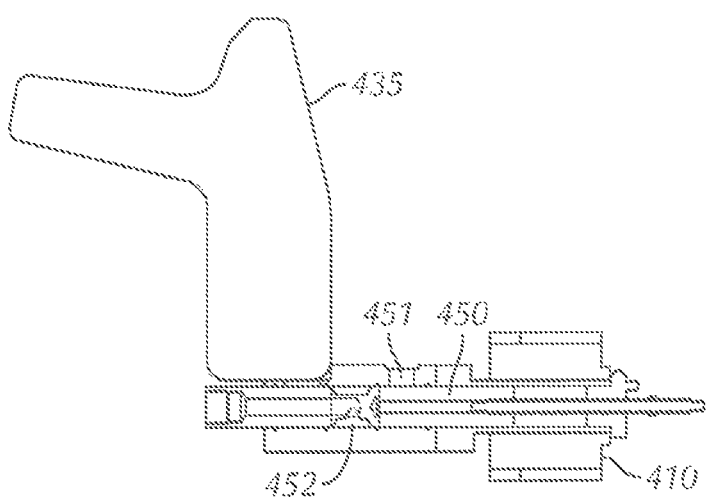
Figure 2C:
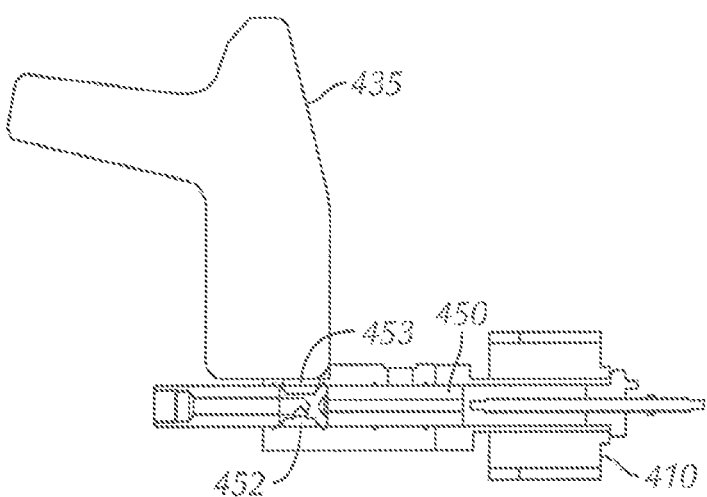

Referring now to FIGS. 2A-C, cross-sectional views of the test chamber and XRF 435 during fill, intermediate, and test positions, respectively, according to embodiments of the present disclosure are shown. In the fill position (FIG. 2A), the slide 450 is in a position to allow fluid to be injected through an injection port 451 into a sample cavity 452. In this embodiment, sample cavity includes approximately a 25 mm opening that allows fluid to flow into the cavity 452. Those of ordinary skill in the art will appreciate that in other embodiments, sample cavity 452 may include openings of different size and/or geometry. One or more of motors (415, 420, or 425 of FIG. 1) may be used to control the orientation of slide 450 within test chamber 410. For example, a motor may move slide 450 laterally in test chamber 410. In the intermediate position (FIG. 2B), slide 450 moves sample cavity 452 including a test fluid out of fluid communication with injection port 451. My moving sample cavity 452 out of fluid communication with injection port 451, fluid is prevented from spilling out of test chamber 410. Thus, the intermediate position may allow the sample size in sample cavity 452 to be controlled. In the test position (FIG. 2C), sample cavity 452 is aligned with test port 453. As sample cavity 452 is not enclosed (enclosing test cavity would prevent accurate XRF analysis), slide 450 should be moved into testing orientation so as to prevent the test fluid from spilling out of sample cavity 452. In the test position, the XRF 435 may be used to analyze the drilling fluid. The sequence of a filling position, an intermediate position, and a test position allows the volume of the sample in sample cavity 452 to be maintained. The sequence also prevents fluid from overflowing from sample cavity 452 as the intermediate position is closed from the rest of the system, thereby preventing the injection side and the testing side of the system to be open at the same time.

Because XRF testing is sensitive to the location of the sample being tested, the motors (415, 420, and 425 of FIG. 1) may be used to ensure that the orientation of sample cavity 452 to XRF 435 is within a specific tolerance. By using an XYZ orientation analysis, the fluid analyzer can ensure that fluid sample tests are not distorted by blockage of the sample, as well as ensure that the sample does not overflow sample cavity 452. Referring briefly back to FIG. 1, in an embodiment wherein motor 415 controls slide 450, slide 450 may be moved laterally within test chamber 410 to move a sample fluid from fluid communication with injection port 451 into orientation with test port 453. During testing, motors 420 and 425 may be configured to change the orientation of either test chamber 410 or XRF 435, thereby allow multiple tests from a single sample to be procured. Because the focal length between the XRF and the sample is important to maintain consistent and comparable results, the motors 415, 420, and 425 may work in concert to ensure that the distance between the sample fluid and test port 453 remains relatively constant. In certain embodiments, the gap between the XRF and the sample may be between 0.5 mm and 1.0 mm. Depending on the specifications of the XRF, this gap may be increased or decreased, thereby allowing the system to be customized to analyze particular fluids. In certain embodiments, the motors may be used to adjust the position of the XRF, thereby allowing multiple samples to be procured. In such an embodiment, the XRF may move in a substantially circular path, thereby allowing various portions of the sample to be tested. Specifically, the XRF may move laterally across the surface of the sample, while maintaining the same height above the sample, thereby allowing various readings to be taken across the surface of the sample. Additionally, because multiple readings of each sample may be procured, false readings may be avoided. For example, in certain embodiments, multiples readings are procured and a statistical average is performed or account for anomalies in the various readings.

Additionally, the temperature of the test chamber 410 and the sample may be controlled, thereby maintaining a constant volume of fluid and allowing the distance between the sample and XRF 435 to be the same among various tests. The temperature may be controlled by disposing a fluid conduit (not shown) in test chamber 410 proximate sample cavity 452. A fluid, such as water, having a known and controlled temperature may be run through the fluid conduit thereby allowing the temperature of the sample fluid to be controlled. Controlling the sample fluid may help ensure that the XRF test is accurate between multiple samples. By controlling the location of the sample relative to XRF 435 and controlling the temperature, the results of the tests may be more accurate and provide better comparability between the results of multiple tests.

Figure 3A:
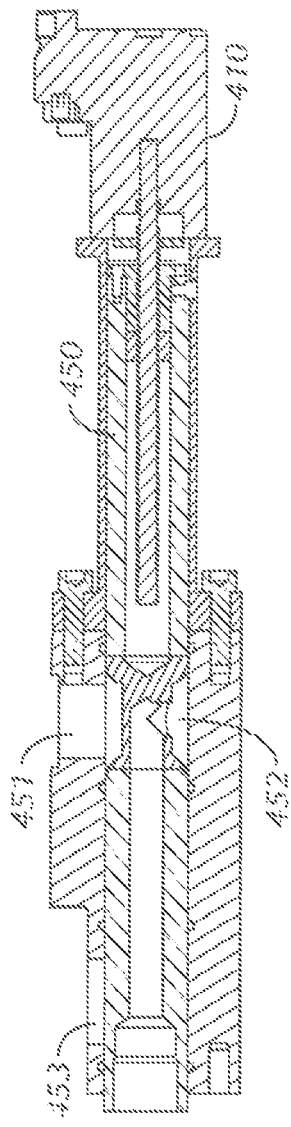
FIGS. 3A-C are cross-sectional views of a test chamber of the XRF analyzer according to embodiments of the present disclosure.
Figure 3B:
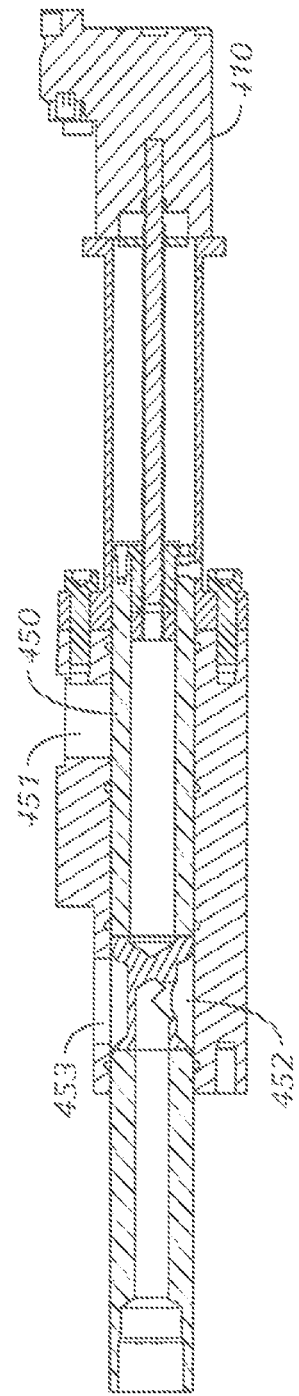
Figure 3C:
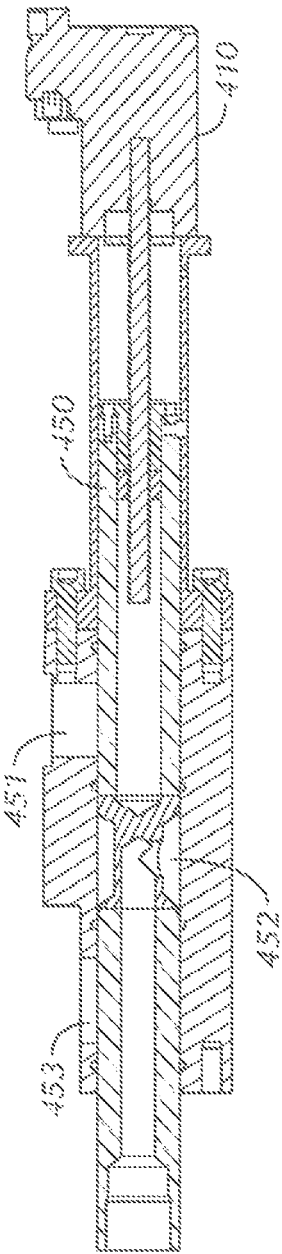

Referring to FIGS. 3A-B, a cross-sectional view of the test chamber in fill and test positions, respectively, according to embodiments of the present disclosure are shown. During a testing process, slide 450 begins in a fill position (FIG. 3A), and a fluid solenoid (not shown) and an air solenoid (not shown) are opened, thereby allowing a sample of fluid to be injected from the active drilling fluid system into sample cavity 452. When sample cavity 452 has the desired volume of fluid, the air and fluid solenoids are closed, thereby stopping the flow of fluid into test chamber 410. Slide 450 is then moved into test position (FIG. 3B), such that sample cavity 452 is aligned with test port 453 and is configured to allow the XRF (not shown) to run a test sequence. After the test sequence, a pump (not shown) is actuated along with opening of the air solenoid, thereby purging sample cavity 452 of the sample fluid. When sample cavity 452 is purged, the pump is stopped and slide 450 is moved back into the fill position. Between the fill position and the test position, the sample may be held in an intermediate position (FIG. 3C). In the intermediate position, the sample may be temporarily held to allow the fluid to stabilize, thereby preventing an overflow. Depending on the properties of the fluid, the hold time may vary, for example, in certain embodiments, the sample is in an intermediate position between 5 seconds and 10 minutes, and in specific embodiments, the sample is in the test position for approximately 30 seconds.

Once in the fill position (FIG. 3A), a base oil cleaner may be injected into test chamber 410 and into sample cavity 452 by opening a base solenoid (not shown). The pump is then re-actuated, thereby purging any residual fluid or particulate matter from test chamber 410. Slide 450 may then be moved back into the test position (FIG. 3B), and the pump actuated via opening of the air solenoid to further remove residual fluid and/or particulate matter from test chamber 410. At this point, a subsequent fluid test may be performed. Those of ordinary skill in the art will appreciate that depending on the type of fluid being tested, the sequence of fill and test positions may vary. For example, in certain operations, only a single purge cycle may be required, while in other operations, three or more purge cycles may be required to adequately purge residual fluid and particulate matter from test chamber 410.

Additional components may be included, such as a valve (not shown) on sample cavity 452, which may be closed when the fluid is being tested. When such a valve is in a closed position, fluid would not be allowed to evacuate sample cavity 452, thereby ensuring the sample volume remains constant. Opening of the valve may allow the fluid to be removed from sample cavity 452, such as during a cleaning cycle. Other components may include cleaning devices. An example of a cleaning device that may be used with embodiments of the present disclosure is a wiper (not shown) disposed on or proximate test chamber 410. The wiper may be used to clean injection port 451, sample cavity 452, or other portions of the system. In certain embodiments, the wiper may be disposed on slide 450, thereby allowing both internal and external components of test chamber 410 to be cleaned. Additionally, a pump (not shown), such as a pneumatic pump may be in fluid communication with sample cavity 452. The pump may be used to draw fluid into or out of sample cavity 452 during filling and cleaning cycles.

During XRF testing, a single sample may be tested multiple times. For example, once in the test position, the XRF 435 may be moved relative to test chamber 410 by actuation of one or more motors, thereby allowing the focus of the XRF to shift relative to sample cavity 452. Because the portion of the sample fluid being tested is small relative to the total surface area of the sample exposed through sample cavity 452, multiple tests not including an overlapping sample portion may be performed. In other embodiments, XRF 435 may be held in a constant position and test chamber 410 may be moved relative to XRF 435, thereby providing another way for multiple tests to be performed. In still another embodiment one or more motors may be used move slide 450 relative to test chamber 410 and/or XRF 435. In such an embodiment, the test chamber 410 and XRF 435 may be held stable, and only slide 410 would be movable.

The XRF analyzer may be combined with the various other testing apparatuses described above, thereby allowing a single fluid analyzer to have a viscometer, electrical stability monitor, and XRF monitor. In such a configuration, the XRF may be disposed either before or after the viscometer or electrical stability monitor, as well as in a configuration to allow the separate tests to occur simultaneously.

Figure 4:
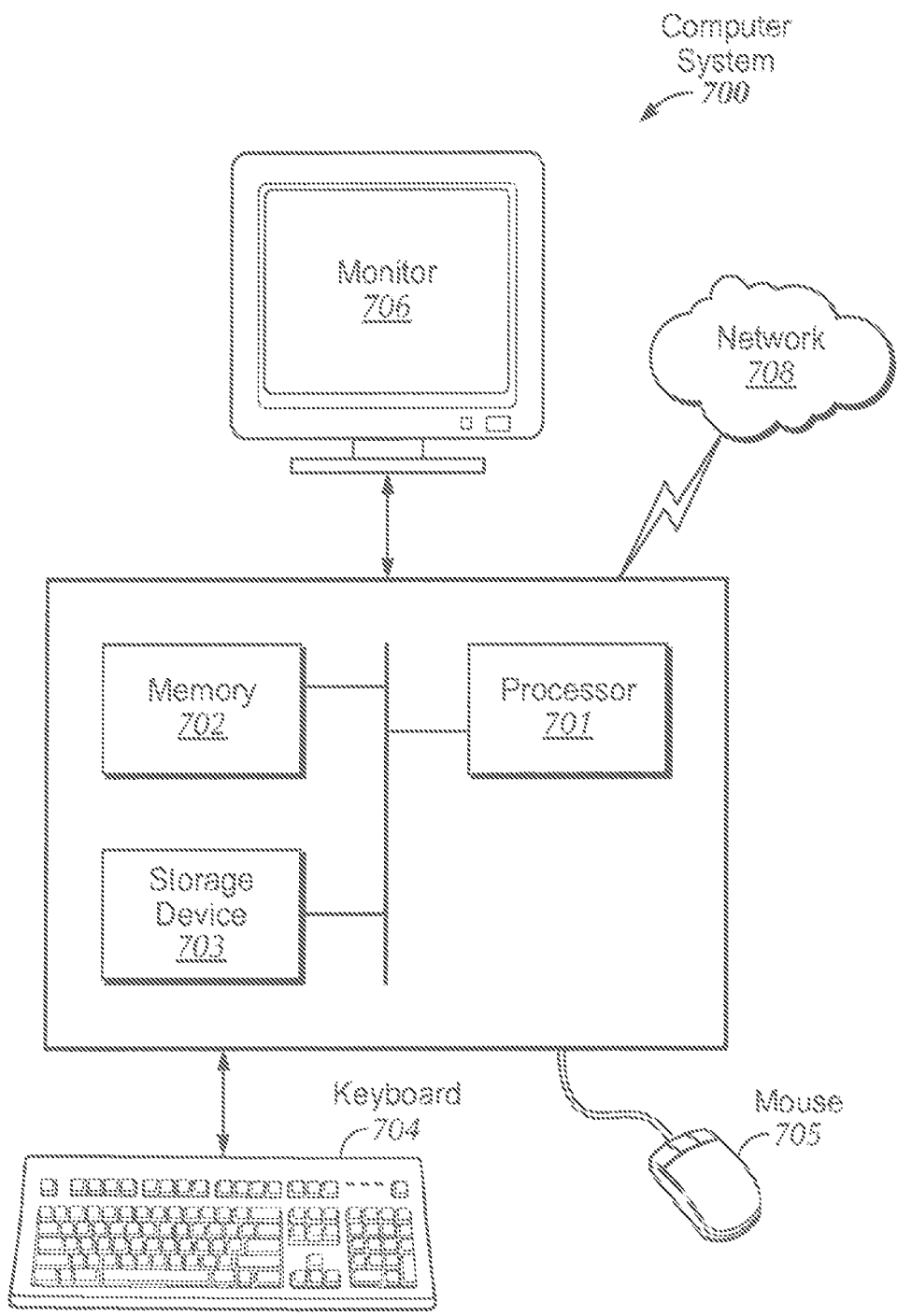
FIG. 4 is a schematic representation of a computer system according to embodiments of the present disclosure.

Embodiments of the present disclosure may be implemented on virtually any type of computer regardless of the platform being used. For example, as shown in FIG. 4, a computer system 700 includes one or more processor(s) 701, associated memory 702 (e.g., random access memory (RAM), cache memory, flash memory, etc.), a storage device 703 (e.g., a hard disk, an optical drive such as a compact disk drive or digital video disk (DVD) drive, a flash memory stick, etc.), and numerous other elements and functionalities typical of today's computers (not shown). In one or more embodiments of the present disclosure, the processor 701 is hardware. For example, the processor may be an integrated circuit. The computer system 700 may also include input means, such as a keyboard 704, a mouse 705, or a microphone (not shown). Further, the computer system 700 may include output means, such as a monitor 706 (e.g., a liquid crystal display (LCD), a plasma display, or cathode ray tube (CRT) monitor). The computer system 700 may be connected to a network 708 (e.g., a local area network (LAN), a wide area network (WAN) such as the Internet, or any other type of network) via a network interface connection (not shown). Those skilled in the art will appreciate that many different types of computer systems exist, and the aforementioned input and output means may take other forms. Generally speaking, the computer system 700 includes at least the minimal processing, input, and/or output means necessary to practice embodiments of the present disclosure.

Further, those skilled in the art will appreciate that one or more elements of the aforementioned computer system 700 may be located at a remote location and connected to the other elements over a network. Further, embodiments of the present disclosure may be implemented on a distributed system having a plurality of nodes, where each portion of the present disclosure (e.g., the local unit at the rig location or a remote control facility) may be located on a different node within the distributed system. In one embodiment of the invention, the node corresponds to a computer system. Alternatively, the node may correspond to a processor with associated physical memory. The node may alternatively correspond to a processor or micro-core of a processor with shared memory and/or resources. Further, software instructions in the form of computer readable program code to perform embodiments of the invention may be stored, temporarily or permanently, on a computer readable medium, such as a compact disc (CD), a diskette, a tape, memory, or any other computer readable storage device.

The computing device includes a processor 701 for executing applications and software instructions configured to perform various functionalities, and memory 702 for storing software instructions and application data. Software instructions to perform embodiments of the invention may be stored on any tangible computer readable medium such as a compact disc (CD), a diskette, a tape, a memory stick such as a jump drive or a flash memory drive, or any other computer or machine readable storage device that can be read and executed by the processor 701 of the computing device. The memory 702 may be flash memory, a hard disk drive (HDD), persistent storage, random access memory (RAM), read-only memory (ROM), any other type of suitable storage space, or any combination thereof.

The computer system 700 is typically associated with a user/operator using the computer system 700. For example, the user may be an individual, a company, an organization, a group of individuals, or another computing device. In one or more embodiments of the invention, the user is a drill engineer that uses the computer system 700 to remotely access a fluid analyzer located at a drilling rig.

Advantageously, embodiments of the present disclosure may provide XRF analysis of drilling fluids during a drilling operation. Because the system may be linked to a computer network, updated results of the XRF analysis may be provided to drilling engineers in real-time or near real-time. Also advantageously, embodiments of the present disclosure may provide an XRF analyzer that takes multiple tests of a fluid sample, thereby providing a drilling engineer a more accurate assessment of the properties of the drilling fluid. Furthermore, the methods and systems disclosed herein may provide a fully automated drilling fluid analysis system that allows fluids to be continuously sampled during drilling, thereby allowing the fluid to be adjusted as required.

Also advantageously, methods according to the present disclosure may allow for the performing and analyzing of larger numbers of data than traditional testing, which may improve the quality and accuracy of the test data. By changing from single point analysis to trend analysis through the use of multiple data points, the accuracy of the resultant data may be further increased. Additionally, methods according to the present disclosure may advantageously allow for the qualitative and quantitative determination of drilling fluid components, which may result in improved resultant data and more efficient drilling.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. An x-ray fluorescence apparatus for measuring properties of a sample fluid, the apparatus comprising:
    a housing having an inlet and an outlet;
    a test chamber disposed within the housing, the test chamber comprising:
        an injection port in fluid communication with the inlet;
        a slide capable of lateral movement within the test chamber, the slide comprising a sample cavity; and
        a test port;
    an x-ray fluorescence spectrometer disposed within the housing, and at least one motor operatively coupled to the slide of the test chamber.

2. The apparatus of claim 1, wherein the at least one motor is configured to move the slide from the injection port to the test port within the test chamber.

3. The apparatus of claim 1, further comprising:
    at least a second motor configured to move at least one of the test chamber and the x-ray fluorescence spectrometer.

4. The apparatus of claim 3, further comprising:
    at least a third motor configured to move at least one of the test chamber and the x-ray fluorescence spectrometer.

5. The apparatus of claim 1, further comprising a cleaning fluid tank in fluid communication with the test chamber.

6. The apparatus of claim 1, further comprising an air source in fluid communication with the test chamber.

7. The apparatus of claim 1, wherein the test chamber further comprises:
a fluid conduit disposed within the test chamber.

8. The apparatus of claim 1, further comprising a pump in fluid communication with the sample cavity.

9. The apparatus of claim 1, further comprising a wiper disposed on the test chamber and configured to contact the injection port.

10. The apparatus of claim 1, further comprising a microprocessor operatively coupled to the x-ray fluorescence spectrometer and the at least one motor.

11. The apparatus of claim 1, further comprising at least one actuated valve and at least one check valve coupled to the test chamber.

12. A method of testing a fluid, the method comprising:
injecting a fluid through an injection port of a test chamber into a sample cavity of a slide capable of lateral movement;
moving the slide laterally from the injection port to a test port of the test chamber;
moving the slide laterally within the test chamber to a test position; and
actuating an x-ray fluorescence spectrometer to sample the fluid within the sample cavity when the slide is in the test position.

13. The method of claim 12, further comprising:
removing the fluid from the sample cavity.

14. The method of claim 13, further comprising:
moving the slide laterally from the test position to a fill position.

15. The method of claim 14, further comprising:
injecting a base fluid through the injection port into the sample cavity.

16. The method of claim 12, further comprising:
moving the test chamber with respect to the x-ray fluorescence spectrometer.

17. The method of claim 12, further comprising:
moving the x-ray fluorescence spectrometer with respect to the test chamber.

18. The method of claim 17, further comprising:
moving the test chamber with respect to the x-ray fluorescence spectrometer.

19. The method of claim 12, further comprising:
adjusting the temperature of the fluid in the sample cavity.

20. The method of claim 12, further comprising:
cleaning the injection port with a wiper.

21. The method of claim 12, wherein the actuating an x-ray fluorescence spectrometer to sample the fluid comprises multiple tests.

* * * * *